(12) United States Patent
Schöck et al.

(10) Patent No.: US 6,433,862 B1
(45) Date of Patent: Aug. 13, 2002

(54) METHOD AND DEVICE FOR TREATING SAMPLES

(75) Inventors: Hans Wilhelm Schöck; Lutz Rose, both of Duisburg (DE)

(73) Assignee: Mannesmann AG, Düsseldorf (DE)

( * ) Notice: Subject to any disclaimer, the term of this patent is extended or adjusted under 35 U.S.C. 154(b) by 0 days.

(21) Appl. No.: 09/434,242

(22) Filed: Nov. 5, 1999

(30) Foreign Application Priority Data

Nov. 6, 1998 (DE) .......................................... 198 52 528

(51) Int. Cl.⁷ .......................... G01N 21/01; G01N 21/63
(52) U.S. Cl. ...................... 356/36; 356/318; 73/864.21; 73/864.81; 73/DIG. 9
(58) Field of Search .......................... 356/36, 317, 318; 73/DIG. 9, 864.21, 864.81

(56) References Cited

FOREIGN PATENT DOCUMENTS

| DE | 3233677 C1 | * 12/1983 |
| JP | 55-134122 | * 10/1980 |

* cited by examiner

*Primary Examiner*—F. L. Evans
(74) *Attorney, Agent, or Firm*—Cohen, Pontani, Lieberman & Pavane

(57) ABSTRACT

A method for analyzing a sample of a steel melt taken from a metallurgical vessel includes taking a sample in a measuring probe, inserting the measuring probe into a holder, and severing the measuring probe at a position of the measuring probe at which the sample is held for producing a measuring probe stub with a severed sample part. The measuring probe stub with the severed sample part is then positioned at an analyzer for analysis. The measuring probe also includes a region for holding slag from the steel melt in the metallurgical vessel.

15 Claims, 5 Drawing Sheets

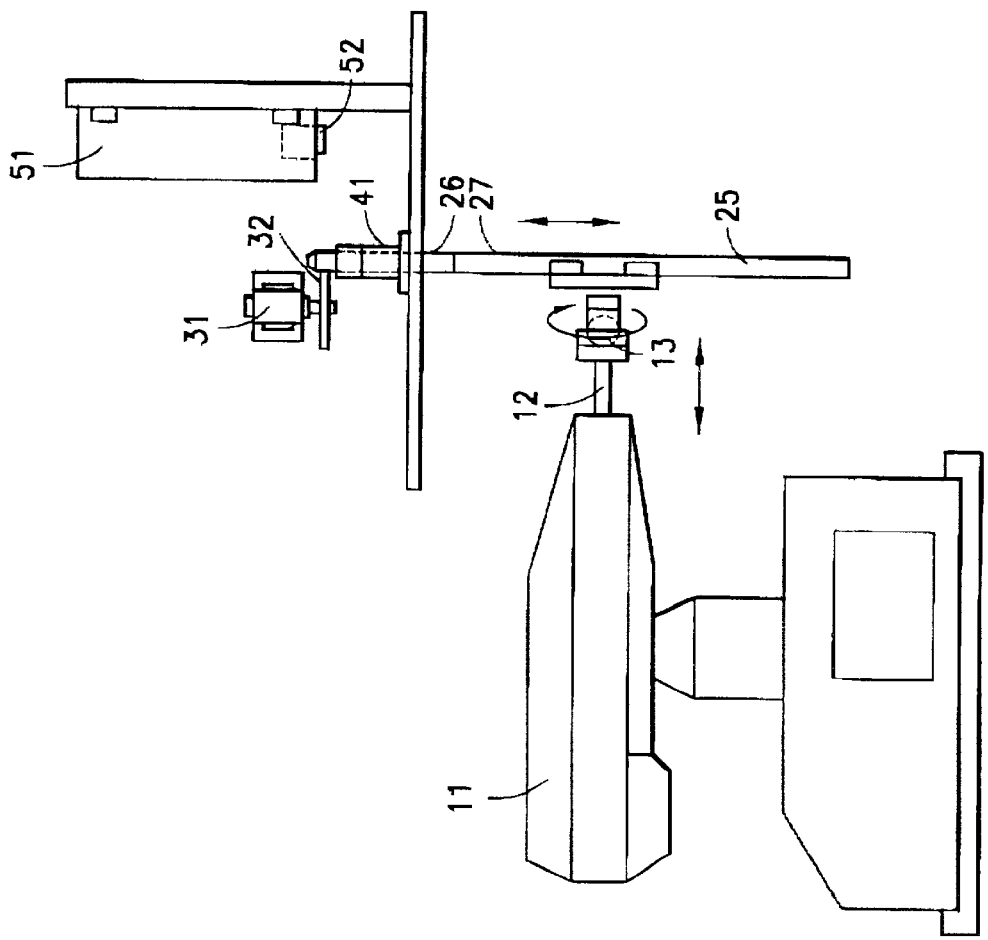
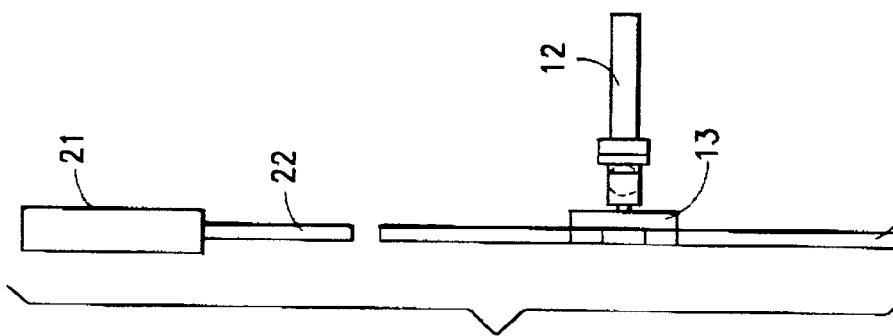

METHOD AND DEVICE FOR TREATING SAMPLES

BACKGROUND OF THE INVENTION

1. Field of the Invention

The invention relates to a method for treating metallurgical samples situated in a measuring probe that is withdrawn from a contact tube of a measuring device using a manipulator after the samples are dipped into a steel melt situated in a metallurgical vessel, and moved to a device for carrying out the method.

2. Description of the Related Art

A prior art Japanese reference JP-A 6-201541 discloses a method for removing samples from a measuring probe in which a parting device is used which cuts out a sub-region containing the sample from the measuring probe. In a subsequent step, the sample is removed from the remaining measuring probe and passed to an analytical device by a pneumatic conveyor.

Valuable time is lost by performing all the steps necessary here before the final analysis of the sample.

SUMMARY OF THE INVENTION

The object of the present invention is to provide a device for analyzing samples, particularly steel samples for converters, in which a minimum of actions is necessary to arrive at the completed analysis.

The object of the invention is achieved by a method for analyzing a sample situated in a measuring probe after being dipped into a metallurgical vessel and removed from a contact tube of a measuring lance, the method comprising the steps of severing the measuring probe at a point of partition in the region in which the sample is situated to produce a measuring probe stub including a severed sample part, passing the measuring probe stub with the severed sample part to an analytical device, and analyzing the severed sample part at the point of partition using the analytical device.

The object is also achieved by a device for analyzing a sample situated in a measuring probe that has been dipped into a steel melt in a metallurgical vessel, comprising a manipulator operatively arranged for gripping the measuring probe and moving the measuring probe to preset positions including a parting position and a first analyzing position, a parting device including a parting tool, a holding device operatively arranged for receiving the measuring probe and holding the measuring probe in the parting position relative to the parting device, the manipulator being operatively arranged for inserting the measuring probe into the holder, the parting device operatively arranged for severing the measuring probe and the sample situated in the measuring probe when the measuring probe is in the parting position thereby producing a measuring probe stub and a severed sample part having a severed surface, and an analytical device comprising an activation device operatively arranged for analyzing the severed surface of the severed sample part when the measuring probe stub is held in a first analyzing position by said manipulator.

According to the invention, the sample is passed to an analytical device, for example an emission spectrometer or a laser analytical device. The analytical device directs an activation beam such, for example, as a laser beam in the case of the laser analytical device, onto the free surface of the sample part still situated in the measuring probe. In preparation for taking samples, the measuring probe has been severed in the region in which the sample is situated, said sample having been severed at the same time, and the measurement probe stub has then been passed, together with the sample part it holds, to the analytical device. When a laser analytical device is used, a plasma is produced here which is used for performing analyses.

The measuring probe, which has been dipped, for example, in a steel melt situated in a converter or other metallurgical vessel, is withdrawn from a contact tube of a measuring lance using a manipulator and passed by the same manipulator directly to a parting station. Without the cut surface of the metal sample being prepared further, this measuring probe is positioned under an analytical device such that the metal sample is activated by an activation beam and an aggregate state is produced at the surface of the metal sample and evaluation of the reflected radiation results in a complete analysis of the steel melt.

The rapid availability of the melt analysis, particularly the determination of the phosphorus content, is crucial to the decision regarding whether tapping is directly possible or whether the melt needs to be treated further.

Advantageously, the measuring probe stub is repositioned such that the slag situated on its outside is likewise passed to the analytical device. When a laser analytical device is used, the laser beam is then directed at various points of the slag layer, a useable plasma being produced for analysis and a sufficiently thick layer of slag being reliably detected. In a specific embodiment, the outer wall of the measuring lance is prepared such that a sufficient quantity of slag adheres to it from the outside in a particularly reliable manner.

Regarding the parting device for severing the measuring probe together with the sample, a mechanical method proposed includes a parting plate and a thermal method proposed includes the use of a plasma beam.

Since inaccuracies may occur, particularly during the transfer by the manipulator, the invention proposes that the exact position of the sample in the measuring probe be located before the measuring probe is severed and that the data be used to position the measuring probe in the parting device.

To perform the method of in-situ analysis of metal and slag melts, the present invention proposes a device with a holding device into which the measuring probe can be vertically inserted by the manipulator. The parting device may be used in the area above the holding device. The measuring device is held by the holding device in a position such that the sample located in the measuring probe is roughly bisected by the parting device. After the measuring probe has been severed, the mouth of the measuring probe stub is moved to the analytical device by the manipulator, the analytical device having a laser device, for example, which can be used to direct the laser beam onto the free surface of the sample situated in the measuring probe stub. After analysis of the metal sample, the manipulator passes the measuring probe stub, and in this case particularly the prepared point of the measuring probe, to the analyzer.

In an advantageous embodiment, the outer wall of the region where the slag samples are taken is processed mechanically, this region being much rougher than the rest of the measuring probe. In a further refinement, the outer wall is treated chemically in the region where the slag samples are taken. A thermally resistant mass having as large a surface as possible is used for this. The invention further proposes a layer of a ceramic compound for this outer wall area.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings, wherein like reference characters denote similar element throughout the several views:

FIG. 1a is a side view of a measuring probe prior to a separation step;

FIG. 1b is a side view of a manipulator holding the measuring probe during the separation step;

DETAILED DESCRIPTION OF THE PRESENTLY PREFERRED EMBODIMENTS

Figure 2:
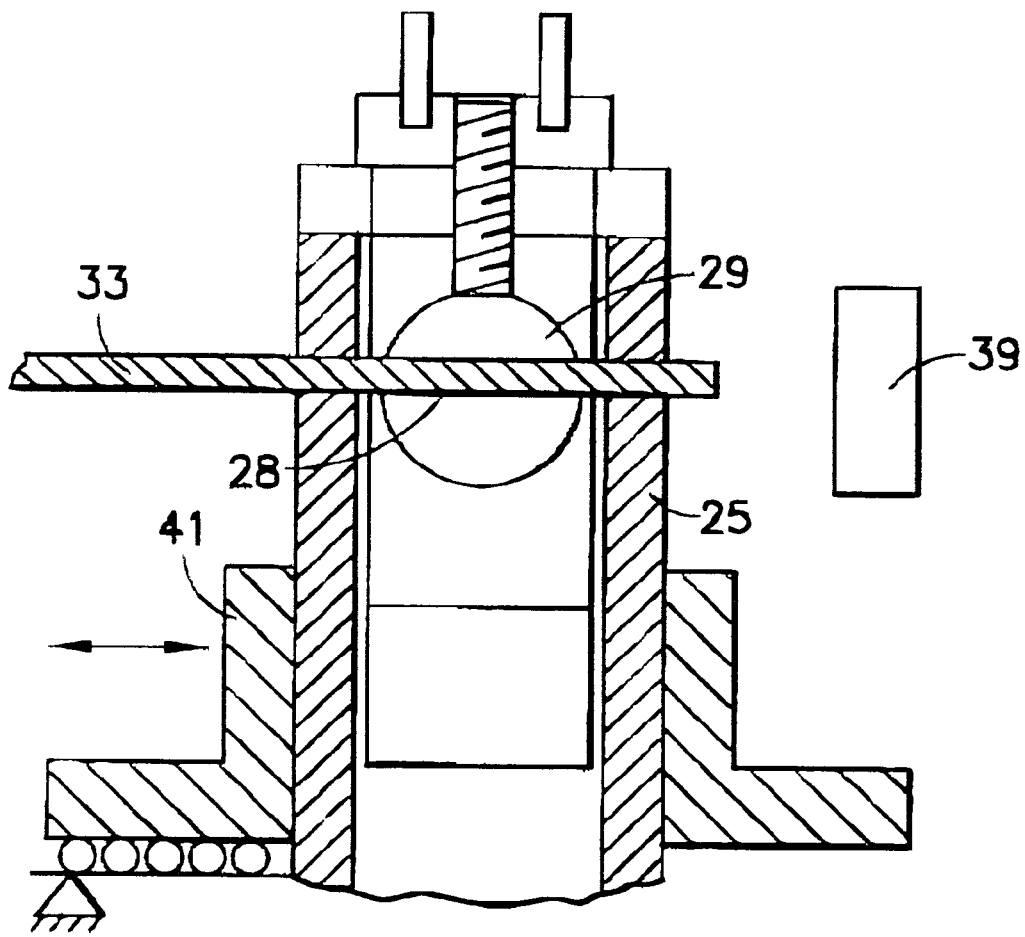
FIG. 2 is a partial sectional view of a measuring probe with a parting device.

FIG. 1a shows a measuring lance 21 from whose contact tube 22 a measuring probe 23 is removed. The measuring lance 21 and contact tube 22 hold the measuring probe 23 while the measuring probe is dipped in a steel melt in a metallurgical vessel such, for example, as a converter. The measuring probe 23 in FIG. 1 has just been removed from the steel melt from which the sample was taken. The measuring probe 23 is in this case gripped by a gripping device 13 arranged on a pivot arm 12 of a manipulator 11 (see FIG. 1b).

In FIG. 1b, the manipulator 11 has guided the measuring probe 23 held by the gripping device 13 on the pivot arm 12 to a holding device 41. Referring also to FIG. 2, in the region of the holding device 41, a parting device 31 with parting tool 32 is arranged for severing the sample 29 (see FIG. 2) such that one half of the sample 29 remains in the measuring probe stub 25 with a free surface 28. Furthermore, a region 26 on the measuring probe stub 25 to which slag preferably sticks is arranged on the outer wall 27 of the measuring probe stub 25.

At a distance within reach of the pivot arm 12, an analytical device 51 is arranged which has an activation device 52 for performing the analysis of the sample 29 and of the slag on the outer wall 27. The analytical device may, for example, include a laser device.

FIG. 2 shows the holding device 41 which firmly holds the measuring probe stub 25 such that the parting tool which, in this case, is a parting plate 33 bisects the sample 29. A detector 39 may be provided to detect the exact position of the measuring probe stub 25 in relation to the parting plate 33.

Figure 3:
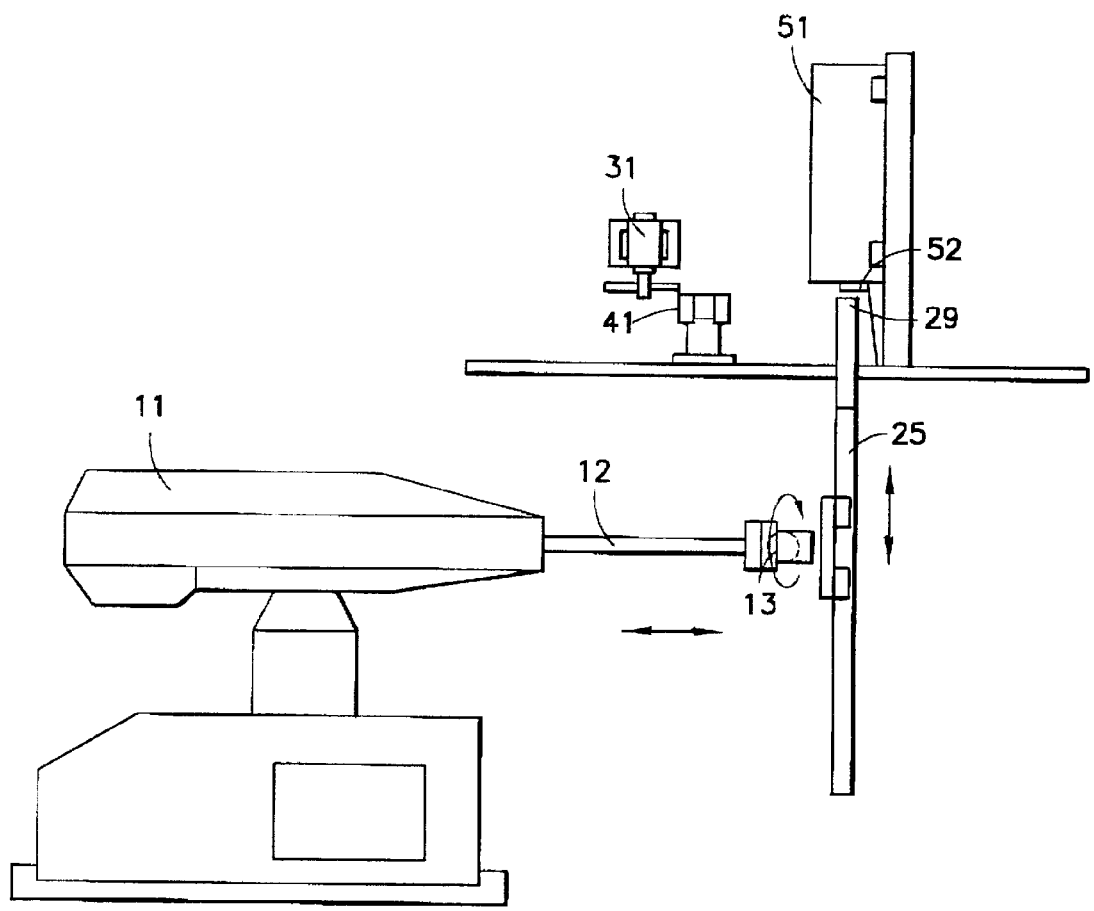
FIG. 3 is a side view of the manipulator holding the measuring probe during a sample analysis step.

In FIG. 3, the pivot arm 12 of the manipulator 11 has been used to move the measuring probe stub 25 to the analytical device 51. The measuring probe stub 25 is positioned such that the free surface 28 (see FIG. 2) of the sample 29 corresponds with, i.e., exposed to, the activation device 52.

Figure 4:
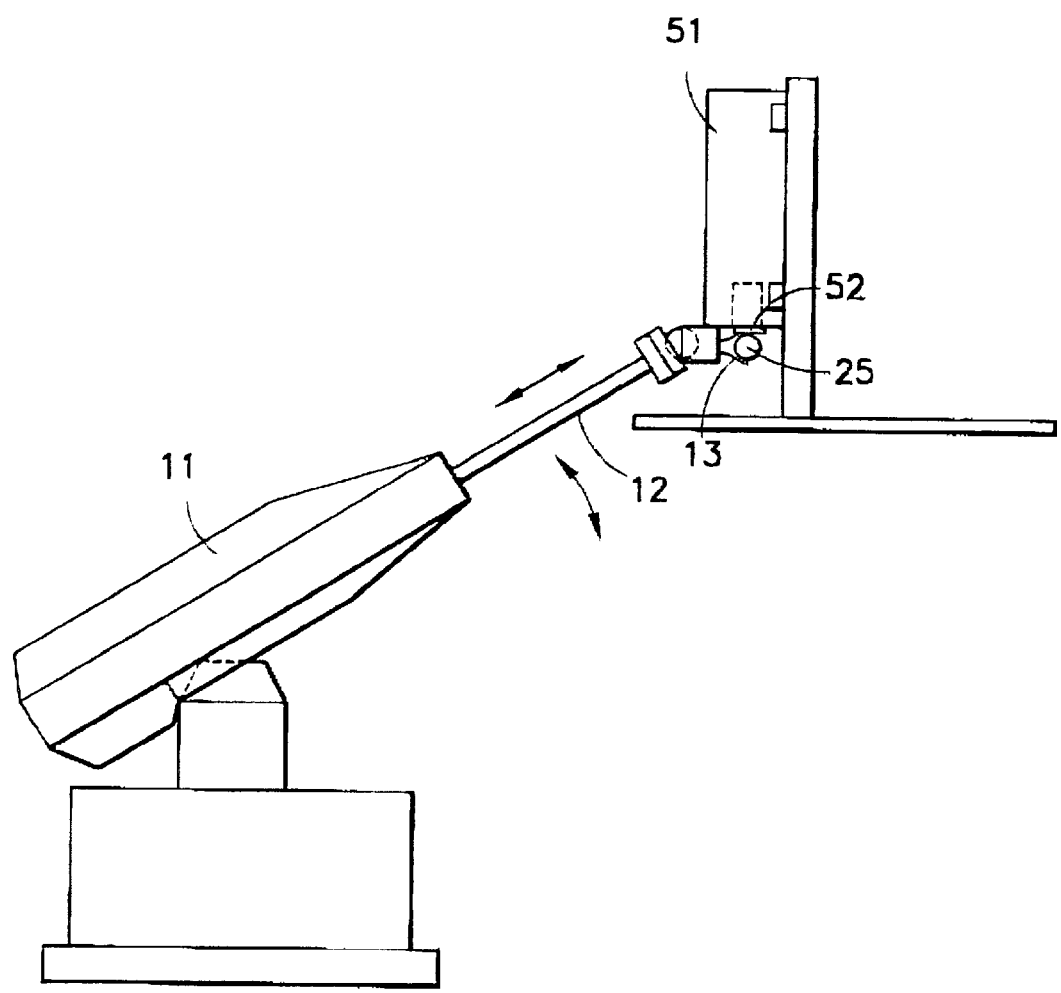
FIG. 4 is a side view of the manipulator holding the measuring probe during a slag analysis step.

In FIG. 4, the manipulator 11 is pivoted such that the gripping device 13 mounted on the pivot arm 12 has moved the measuring probe stub 25 to a horizontal position and moved it relative to the analytical device 51 such that the outer wall 27 of the measuring probe stub 25 corresponds, i.e., is exposed to, the activation device 52.

Figure 5:
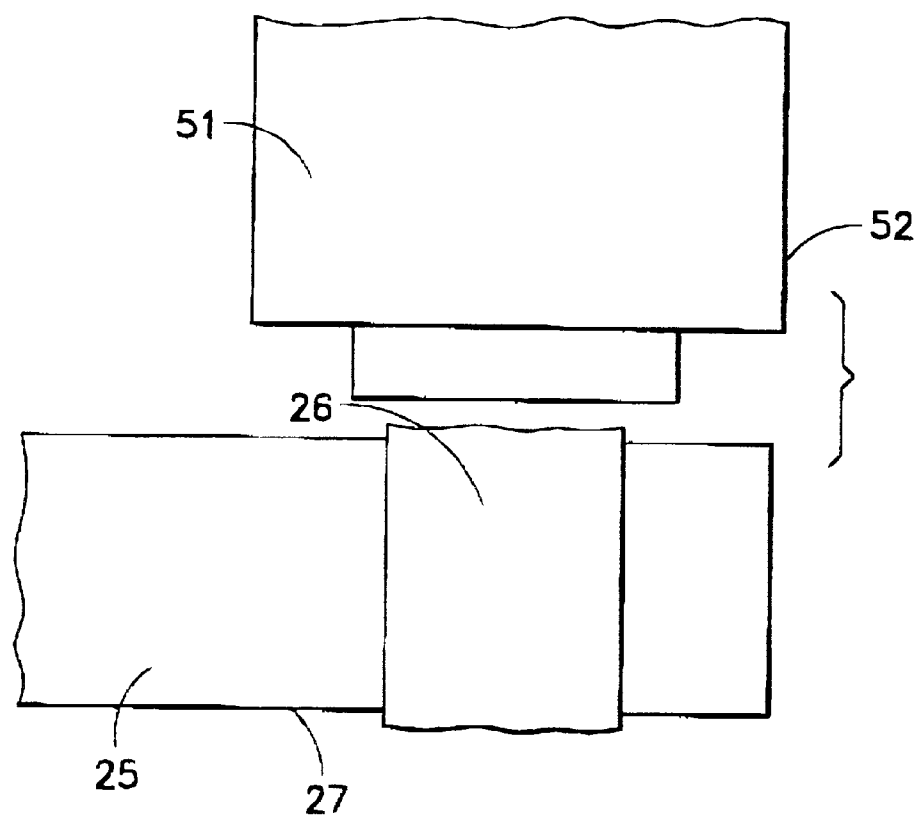
FIG. 5 is a detailed view of a slag region of the measuring probe.

FIG. 5 is a detailed illustration of how the measuring probe stub 25 includes an outer wall 27 with a region 26 on which slag has collected to a particular degree. In FIG. 5, the region 26 with the slag is in position relative to the activation device 52 on the analytical device 51.

The invention is not limited by the embodiments described above which are presented as examples only but can be modified in various ways within the scope of protection defined by the appended patent claims.

We claim:

1. A method for analyzing a sample situated in a measuring probe after being dipped into a metallurgical vessel and removed from a contact tube of a measuring lance, said method comprising the steps of:
   (a) severing the measuring probe at a point of partition in the region in which the sample is situated to produce a measuring probe stub including a severed sample part;
   (b) passing the measuring probe stub with the severed sample part to an analytical device; and
   (c) analyzing the severed sample part at the point of partition using the analytical device.

2. The method of claim 1, further comprising the following steps:
   (d) repositioning the measuring probe stub such that slag situated on an outer side is passed to the analytical device; and
   (e) analyzing various points of the slag layer using the analytical device.

3. The method of claim 1, wherein said step (a) comprises severing the measuring probe thermally using a plasma beam.

4. The method of claim 1, further comprising the steps of:
   (i) locating a position of the sample in the measuring probe; and
   (ii) using the position data to position the measuring probe in the parting device for performing said step (a).

5. A device for analyzing a sample situated in a measuring probe that has been dipped into a steel melt in a metallurgical vessel, comprising:
   a manipulator operatively arranged for gripping the measuring probe and moving the measuring probe to preset positions including a parting position and a first analyzing position;
   a parting device including a parting tool;
   a holding device operatively arranged for receiving the measuring probe and holding the measuring probe in the parting position relative to said parting device, said manipulator being operatively arranged for inserting said measuring probe into said holder, said parting device operatively arranged for severing said measuring probe and the sample situated in said measuring probe when said measuring probe is in said parting position thereby producing a measuring probe stub and a severed sample part having a severed surface; and
   an analytical device comprising an activation device operatively arranged for analyzing said severed surface of said severed sample part when said measuring probe stub is held in a first analyzing position by said manipulator.

6. The device of claim 5, wherein said analytical device comprises an emission spectrometer.

7. The device of claim 5, wherein the analytical device comprises a laser device operatively arranged for directing a laser beam onto the severed surface of said severed sample part when said measuring probe stub is in said first analyzing position.

8. The device of claim 5, wherein said manipulator is further operatively arranged for moving said measuring probe stub to a second analytical position in which said activation device analyzes a region of an outer wall of said measuring probe, said region comprising slag from the metallurgical vessel.

9. The device of claim 5, wherein said parting tool of said parting device comprises a parting plate.

10. The device of claim 5, wherein said parting tool of said parting device comprises a laser device.

11. The device of claim 5, further comprising a detector operatively arranged in a region of said parting device for determining a position of the sample in the measuring probe before the measuring probe is severed by said parting device.

12. The device of claim 5 further comprising the measuring probe, wherein said measuring probe is operatively arranged for use with a measuring lance for dipping into a steel melt situated in a metallurgical vessel and taking samples at a sample position from the steel melt, said measuring probe comprising a region in a vicinity of the sample position on an outer wall of said measuring probe being prepared such that, after it is dipped into the melt, an amount of slag adheres to said region of said outer wall which is sufficient for taking samples.

13. The device of claim 12, wherein said region of said outer wall of said measuring probe is mechanically processed so that said region of said outer wall has a different roughness than the remainder of said outer surface for taking samples of the slag.

14. The device of claim 12, wherein said region of said outer wall of said measuring probe is chemically treated for taking samples of the slag.

15. The device of claim 14, wherein said outer wall of said measuring probe comprises a ceramic mass layer.

* * * * *